United States Patent [19]

Lin

[11] Patent Number: 5,539,131

[45] Date of Patent: Jul. 23, 1996

[54] OLEFIN EPOXIDATION PROCESS

[75] Inventor: Shaw-Chan Lin, West Chester, Pa.

[73] Assignee: ARCO Chemical Technology, L.P., Greenville, Del.

[21] Appl. No.: 501,858

[22] Filed: Jul. 13, 1995

[51] Int. Cl.$^6$ .................... C07D 301/19; C07D 303/04
[52] U.S. Cl. .................... 549/529; 568/571; 568/576
[58] Field of Search ............................ 549/529; 568/571, 568/576

[56] References Cited

U.S. PATENT DOCUMENTS

| | | |
|---|---|---|
| 2,845,461 | 7/1958 | Winkler et al. |
| 3,351,635 | 11/1967 | Kollar. |
| 3,360,584 | 12/1967 | Kollar ................................ 568/571 |
| 3,478,108 | 11/1969 | Grane et al. |
| 3,665,047 | 5/1972 | Gislon et al. ........................ 568/571 |
| 3,907,902 | 9/1975 | Grane. |
| 4,891,437 | 1/1990 | Marquis et al. ..................... 549/529 |
| 5,104,493 | 4/1992 | Chong ................................ 568/576 |
| 5,220,075 | 6/1993 | Ember ................................ 568/571 |
| 5,436,376 | 7/1995 | Shev et al. .......................... 549/529 |

FOREIGN PATENT DOCUMENTS 799503  11/1968  Canada ........................... 549/529

OTHER PUBLICATIONS

R. A. Sheldon, Journal of Molecular Catalyses, 7, pp. 107–126 (1980) "Synthetic and Mechanistic Aspects of Metal–Catalyzed Epoxidations with Hydroperoxides".

*Primary Examiner*—Joseph E. Evans
*Attorney, Agent, or Firm*—William C. Long

[57] ABSTRACT

In the Oxirane process for epoxide production, at least part of the alcohol formed during isobutane or isopentane peroxidation is replaced by an inert solvent such as decane.

5 Claims, 1 Drawing Sheet

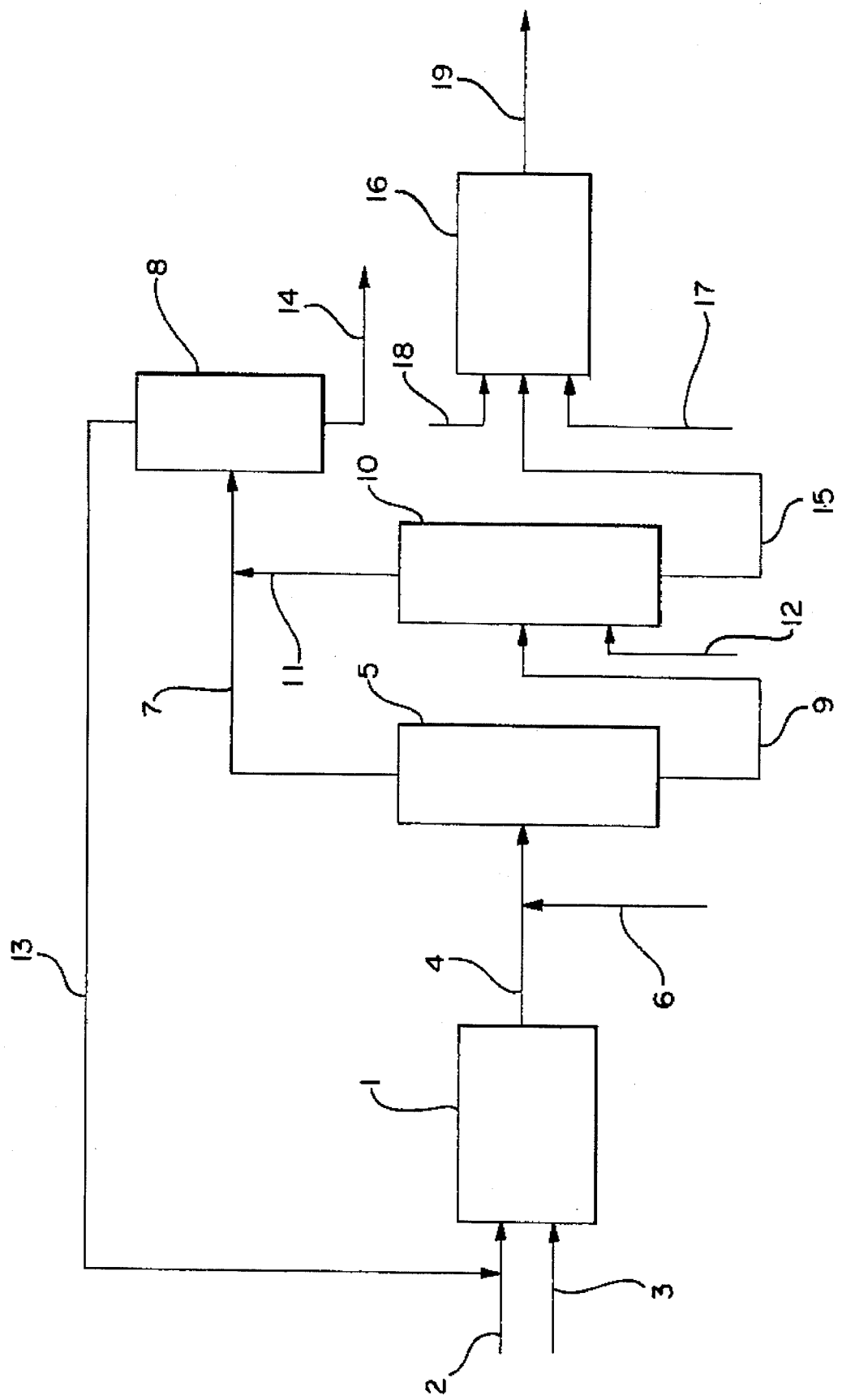

OLEFIN EPOXIDATION PROCESS

BACKGROUND OF THE INVENTION

1. Field of the Invention

A commercial process for the production of epoxides comprises oxidizing an isoalkane such as isobutane to form a mixture of the corresponding hydroperoxide, e.g. tertiary butyl hydroperoxide, and alcohol, e.g. tertiary butanol, and contacting the mixture with an olefin in the presence of a suitable catalyst to form the epoxide. In the improvement of this invention, alcohol formed during the hydrocarbon peroxidation is replaced in whole or in part with an inert solvent such as decane prior to use of the hydroperoxide in the epoxidation reaction; substantial improvements in epoxidation reaction rate and selectivity are achieved.

2. Description of the Prior Art

The basic patent covering this technology is U.S. Pat. No. 3,351,635. This patent describes the reactants, reaction conditions, catalysts, and the like which are useful in the process. Although the patent describes the use of various solvents including hydrocarbons in the epoxidation most usually the components of the peroxidation reaction mixture comprised of the hydroperoxide and the corresponding alcohol are used directly in the epoxidation without the addition of extraneous solvents. See for example, U.S. Pat. No. 4,891,437 which emphasizes highly polar reaction mixtures and which requires high concentrations of hydroperoxide, the corresponding alcohol and product epoxide in the epoxidation reaction system.

R. A. Sheldon, *Journal of Molecular Catalyses*, 7, pages 107–126 (1980) "Synthetic and Mechanistic Aspects of Metal-Catalyzed Epoxidations with Hydroperoxides" teaches that polar solvents, particularly alcohols and water greatly retard the epoxidation and that auto-retardation by coproduct alcohol is observed.

An important consideration in carrying out the epoxidation reaction is the avoidance of high concentrations of hydroperoxide and the potential hazards associated therewith.

BRIEF DESCRIPTION OF THE INVENTION

In accordance with the present invention, the composition of the feed mixture to the epoxidation reaction, exclusive of olefin, is adjusted to meet certain criteria. Specifically, the weight ratio of hydroperoxide to corresponding alcohol in the feed mixture is at least $\frac{1}{1}$ and preferably at least $\frac{2}{1}$, the weight percentage of hydroperoxide in the feed is not more than 70%, preferably not more than 50%, and an inert solvent component is provided in at least amount sufficient to comprise 10% or more by weight of the feed exclusive of olefin.

DESCRIPTION OF THE DRAWING

The accompanying drawing illustrates in schematic form a practice of the invention.

DETAILED DESCRIPTION

In one embodiment of the invention, the peroxidation of the isoalkane is carried out at low conversions in order to provide a product mixture having a high hydroperoxide to alcohol ratio. In such cases, after isoalkane removal, sufficient inert solvent is added to meet the criteria described above prior to introduction of the mixture into the epoxidation reaction zone.

More commonly, however, the isoalkane peroxidation is carried to higher conversions such that the hydroperoxide to alcohol product ratio is less than $\frac{1}{1}$ and in such cases according to the invention at least a portion of the alcohol is removed from the peroxidation reaction mixture and inert solvent added to form a feed to the epoxidation meeting the above criteria.

Practice of the invention is applicable to systems involving peroxidation of isobutane or isopentane. Because of the relatively low boiling points of these hydrocarbons, it is customary to separate unreacted hydrocarbon from the peroxidation reaction mixture prior to use of the mixture of peroxidation products in the epoxidation.

The invention can be described with respect to the accompanying drawing which illustrates propylene oxide production by reaction of propylene with tertiary butyl hydroperoxide in accordance with the invention.

Referring to the drawing, isobutane is oxidized in reaction zone 1 in accordance with well known and conventional procedures to form tertiary butyl hydroperoxide. Isobutane is introduced via line 2 and molecular oxygen via line 3. Reaction conditions are as described, for example, in U.S. Pat. No. 2,845,461, 3,478,108 and 3,907,902.

The reaction mixture from zone 1 comprises unreacted isobutane, tertiary butyl hydroperoxide and tertiary butanol. Generally, tertiary butyl hydroperoxide and tertiary butanol are produced in close to equal amounts by weight although this can vary considerably.

From zone 1, the peroxidation reaction mixture passes via line 4 to high pressure debutanizer 5 for separation of unreacted isobutane. As an essential feature of the invention, an inert solvent such as decane is fed to column 5 via line 6 in amount sufficient to insure that the tertiary butyl hydroperoxide concentration in the column bottoms does not exceed 70 wt %. An overhead stream mainly comprised of isobutane passes from column 5 via line 7 to $C_4$ splitter column 8 while a bottoms stream comprised of tertiary butyl hydroperoxide, tertiary butanol, remaining unreacted isobutane and inert solvent passes via line 9 to low pressure debutanizer 10.

In debutanizer 10 essentially all of the remaining unreacted isobutane is separated overhead via line 11 together with tertiary butanol as well as a substantial portion of the water formed in the isobutane peroxidation. Sufficient tertiary butanol is separated overhead so that the weight ratio of tertiary butyl hydroperoxide to tertiary butanol in the bottoms stream is at least $\frac{1}{1}$, preferably at least $\frac{2}{1}$.

Inert solvent decane is introduced into debutanizer 10 via line 12 to provide for sufficient dilution in the bottoms such that the tertiary butyl hydroperoxide concentration in the bottoms does not exceed 70 wt %. An added benefit of addition of decane is the fact that the amount of water distilled overhead is significantly increased due to the presence of the added decane so that subsequent use of the bottoms in epoxidation results in substantially lower glycol formation.

Overhead from debutanizer 10 passes to splitter 8 via line 11. In splitter 8, the predominance of the isobutane is separated overhead via line 13 and recycled to zone 1. Bottoms from splitter 8 is removed via line 14 and can be further treated for recovery of the various components or used as fuel.

The bottoms stream from debutanizer 10 passes via line 15 to epoxidation zone 16 wherein it is reacted with propylene to form propylene oxide. Propylene is introduced into zone 16 via line 17, and molybdenum catalyst is introduced via line 18. The reaction in zone 16 is carried out as described in basic U.S. Pat. No. 3,351,635. The epoxidation reaction product mixture is removed via line 19 and is worked up in accordance with conventional procedures. Decane solvent is recovered by distillation and is recycled to debutanizers 5 and 10 (not shown).

Through practice of the invention as compared to prior practices using tertiary butanol as solvent rather than an added inert material, the rate of epoxidation reaction in reaction zone 16 is markedly increased, as much as 50% for a doubling of the tertiary butyl hydroperoxide to tertiary butanol weight ratio, while the reaction selectivity is improved by a significant amount. At the same time the hazards of dealing with hydroperoxide concentration above 70 wt % are avoided.

Although decane is the preferred inert solvent, other solvents can be employed. Alkanes having about 8–20 carbon atoms can be used, as can cycloaliphatic alcohols such as cyclohexanol. Gamma butyrolactone can also be used. Decane is, however, preferred.

The following examples illustrate practice of the invention with reference to the attached drawing.

EXAMPLE I

Isobutane is non-catalytically oxidized in reactor 1 with molecular oxygen under conventional conditions to form tertiary butyl hydroperoxide. The oxidation reaction mixture comprised by weight of 54.7% isobutane, 0.5% n-butane, 18.0% tertiary butanol, 26.0% tertiary butyl hydroperoxide, 0.5% water and 0.3% other organics passes at the rate of 100 lbs/hr via line 4 to high pressure debutanizer 5. Decane is passed to debutanizer 5 via line 6 at the rate of 7 lbs/hr.

An overhead stream is removed at the rate of 49.2 lbs/hr from debutanizer 5 via line 7 at 129° F. and 110 psia comprised by weight of 98.85% isobutane, 0.81% n-butane, 0.003% tertiary butyl hydroperoxide, 0.16% tertiary butanol, 0.17% water and traces of other organics. This stream passes via line 7 to splitter 8.

A bottoms stream is removed from debutanizer 5 at the rate of 57.8 lbs/hr via line 9 at 240° F. and 120 psia comprised by weight of 10.45% isobutane, 0.18% n-butane, 31.01% tertiary butanol, 45% tertiary butyl hydroperoxide, 0.72% water, 0.52% other ogranics, and 12.11% decane. This stream passes via line 9 to low pressure debutanizer 10 to which 10.0 lbs/hr of decane is also introduced via line 12.

An overhead containing essentially all the remaining isobutane and n-butane and most of the water fed to debutanizer 10 is removed via line 11 and passes to splitter 8. The bottoms is removed from debutanizer 10 at the rate of 57.8 lbs/hr via line 15 at 240° F. and 20 psia and comprises by weight essentially nil isobutane and n-butane, 24.86% tertiary butanol, 45% tertiary butyl hydroperoxide, 0.22% water, 0.49% other organics and 29.42% decane. The tertiary butyl hydroperoxide concentration is 45 wt % and the ratio of tertiary butyl hydroperoxide to tertiary butanol is 1.81/1.

The bottoms stream passes via line 15 to epoxidation reactor 16 at the rate of 57.8 lbs/hr wherein it is reacted at 248° F. and 500 psia with propylene which is introduced via line 17 at the rate of 43 lbs/hr. Soluble molybdenum catalyst is added via line 18 to provide 108 ppm concentration as Mo in zone 16. Hydroperoxide conversion in zone 16 is 99%, selectivity to propylene oxide is 92.3%. Contrasted to a similar system where decane is replaced by an equivalent amount by weight of tertiary butanol as in conventional practice, a 50% reaction rate increase is achieved through practice of the invention at a selectivity which is 1.8% higher.

The epoxidation mixture passes from reactor 16 via line 19 and the various components are recovered by a conventional distillation sequence.

Comparative Example A

This example illustrates a process similar to that described in Example A but without decane addition.

Isobutane is non-catalytically oxidized in reactor 1 with molecular oxygen under conventional conditions to form tertiary butyl hydroperoxide. The oxidation reaction mixture comprised by weight of 54.7% isobutane, 0.5% n-butane, 18.0% tertiary ;butanol, 26.0% tertiary butyl hydroperoxide 0.5% water and 0.3% other organics passes at the rate of 100 lbs/hr via line 4 to high pressure debutanizer 5. Tertiary butanol is passed to debutanizer 5 via line 6 at the rate of 7 lbs/hr.

An overhead stream is removed from debutanizer 5 at the rate of 49.2 lb/hr via line 7 at 129° F. and 110 psia comprised by weight of 98.8% isobutane, 0.81% n-butane, 0.002% tertiary butyl hydroperoxide, 0.18% tertiary butanol, 0.13% water and traces of other organics. This stream passes via line 7 to splitter 8.

A bottoms stream is removed from debutanizer 5 at the rate of 57.8 lbs/hr via line 9 at 222° F. and 120 psia comprised by weight of 10.42% isobutane, 0.18% n-butane, 43.11% tertiary butanol, 45% tertiary butyl hydroperoxide, 0.76% water, and 0.52% other organics. This stream passes via line 9 to low pressure debutanizer 10 to which 10.0 lbs/hr of tertiary butanol is also introduced via line 12.

An overhead containing essentially all the remaining isobutane and n-butane and some of the water fed to debutanizer 10 is removed via line 11 and passes to splitter 8. The bottoms is removed from debutanizer 10 at the rate of 57.8 lbs/hr via line 15 at 220° F. and 20 psia and comprises by weight essentially nil isobutane and n-butane, 54.02% tertiary butanol, 45% tertiary butyl hydroperoxide, 0.47% water, and 0.5% other organics. The tertiary butyl hydroperoxide concentration is 45 wt % and the ratio of tertiary butyl hydroperoxide to tertiary butanol is 0.83/1.

The bottoms stream passes via line 15 to epoxidation reactor 16 wherein it is reacted at 248° F. and 500 psia with propylene which is introduced via line 17 at the rate of 43 lbs/hr. Soluble molybdenum catalyst is added via line 18 to provide 108 ppm concentration as Mo in zone 16. Hydroperoxide conversion in zone 16 is 99%, selectivity to propylene oxide is 90.5%. Contrasted to the process of Example 1, reaction rate is 50% less and selectivity to propylene oxide is 1.8% less.

The epoxidation mixture passes from reactor 16 via line 19 and the various components are recovered by a conventional distillation sequence.

EXAMPLE 2

Isobutane is non-catalytically oxidized in reactor 1 with molecular oxygen under conventional conditions to form tertiary butyl hydroperoxide. The oxidation reaction mixture comprised by weight of 39.7% isobutane, 0.5% n-butane, 29.0% tertiary butanol, 29.0% tertiary butyl hydroperoxide, 1.10% water and 0.7% other organics passes at the rate of 100 lbs/hr via line 4 to high pressure debutanizer 5. Decane is passed to debutanizer 5 via line 6 at the rate of 7 lbs/hr.

An overhead stream is removed from debutanizer 5 at the rate of 42.6 lbs/hr via line 7 at 133° F. and 110 psia comprised by weight of 91.03% isobutane, 1.13% n-butane, 0.06% tertiary butyl hydroperoxide, 6.84% tertiary butanol, 0.89% water and traces of other organics. This stream passes via line 7 to splitter 8.

A bottoms stream is removed from debutanizer 5 at the rate of 64.4 lbs/hr via line 9 at 326° F. and 120 psia comprised by weight of 1.41% isobutane, 0.03% n-butane, 40.51% tertiary butanol, 45% tertiary butyl hydroperoxide, 1.12% water, 1.06% other organics, and 10.87% decane. This stream passes via line 9 to low pressure debutanizer 10 to which 10.0 lbs/hr of decane is also introduced via line 12.

An overhead containing essentially all the remaining isobutane and n-butane and most of the water fed to debutanizer 10 is removed via line 11 and passes to splitter 8. The bottoms is removed from debutanizer 10 at the rate of 64.4 lbs/hr via line 15 at 238° F. and 20 psia and comprises by weight essentially nil isobutane and n-butane, 27.39% tertiary butanol, 45% tertiary butyl hydroperoxide, 0.26% water, 0.95% ether organics and 26.40% decane. The tertiary butyl hydroperoxide concentration is 45 wt% and the ratio of tertiary butyl hydroperoxide to tertiary butanol is 1.64/1.

The bottoms stream passes via line 15 to epoxidation reactor 16 wherein it is reacted at 248° F. and 500 osia with propylene which is introduced via line 17 at the rate of 43 lbs/hr. Soluble molybdenum catalyst is added via line 18 to provide 108 ppm concentration as Mo in zone 16. Hydroperoxide conversion in zone 16 is 99%, selectivity to propylene oxide is 90.8%. Contrasted to the similar system of comparative Example B where decane is replaced by an equivalent amount by weight of tertiary butanol as in conventional practice, 46% reaction rate increase is achieved through practice of the invention at a selectivity which is 2.6% higher.

The epoxidation mixture passes from reactor 16 via line 19 and the various components are recovered by a conventional distillation sequence.

Comparative Example B

This example illustrates a process similar to that of Example 2 but without decane addition.

Isobutane is non-catalytically oxidized in reactor 1 with molecular oxygen under conventional conditions to form tertiary butyl hydroperoxide. The oxidation reaction mixture comprised by weight of 37.70% isobutane, 0.5% n-butane, 29.0% tertiary butanol, 29.0% tertiary butyl hydroperoxide 1.10% water and 0.7% other organics passes at the rate of 100 lbs/hr via line 4 to high pressure debutanizer 5. Tertiary butanol is passed to debutanizer 5 via line 6 at the rate of 7 lbs/hr.

An overhead stream is removed from debutanizer 5 at the rate of 42.6 lbs/hr via line 7 at 133° F. and 110 psia comprised by weight of 91.2% isobutane, 1.14% n-butane, 0.04% tertiary butyl hydroperoxide, 6.87% tertiary butanol, 0.7% water and traces of other organics. This stream passes via line 7 to splitter 8.

A bottoms stream is removed from debutanizer 5 at the rate of 64.4 lbs/hr via line 9 at 319° F. and 120 psia comprised by weight of 1.31% isobutane, 0.03% n-butane, 51.35% tertiary butanol, 45% tertiary butyl hydroperoxide, 1.24% water, and 1.07% other organics. This stream passes via line 9 to low pressure debutanizer 10 to which 10.0 lbs/hr of tertiary butanol is also introduced via line 12.

An overhead containing essentially all the remaining isobutane and n-butane and some of the water fed to debutanizer 10 is removed via line 11 and passes to splitter 8. The bottoms is removed from debutanizer 10 at the rate of 64.4 lbs/hr via line 15 at 219° F. and 20 psia and comprises by weight essentially nil isobutane and n-butane, 53.39% tertiary butanol, 45% tertiary butyl hydroperoxide, 0.62% water and 0.98% other organics. The tertiary butyl hydroperoxide concentration is 45% wt and the ratio of tertiary butyl hydroperoxide to tertiary butanol is 0.84/1.

The bottoms stream passes via line 15 to epoxidation reactor 16 wherein it is reacted at 248° F. and 500 psia with propylene which is introduced via line 17 at the rate of 43 lbs/hr. Soluble molybdenum catalyst is added via line 18 to provide 108 ppm concentration as Mo in zone 16. Hydroperoxide conversion in zone 16 is 99%, selectivity to propylene oxide is 88.2%. Contrasted to the system of Example 2 reaction rate is 46% less and selectivity to propylene oxide is 2.6% less.

The epoxidation mixture passes from reactor 16 via line 19 and the various components are recovered by a conventional distillation sequence.

I claim:

1. In a process for the production of propylene oxide wherein isobutane or isopentane is oxidized by reaction with molecular oxygen to form a reaction mixture containing both the corresponding hydroperoxide and alcohol, the improvement which comprises adding an inert solvent alkane having 8–20 carbon atoms to said mixture and distilling the resulting mixture to separate alcohol overhead from a bottoms stream comprised of said hydroperoxide, the amount of solvent added being sufficient to provide solvent in amount of at least 10 wt % in the bottoms stream, the amount of alcohol removed as overhead being sufficient to increase the weight ratio of hydroperoxide to alcohol in said bottoms stream to at least 2/1, the distillation being carried out under conditions such that the hydroperoxide concentration in the bottoms stream does not exceed 70 wt %, and catalytically reacting propylene with the hydroperoxide in said bottoms stream to form propylene oxide.

2. The process of claim 1 wherein isobutane is oxidized.

3. The process of claim 1 wherein isopentane is oxidized.

4. The process of claim 1 wherein the inert solvent is an alkane having 8–20 carbon atoms.

5. The process of claim 1 wherein the inert solvent is decane.

* * * * *